United States Patent

Gypser et al.

(10) Patent No.: US 6,593,315 B2
(45) Date of Patent: Jul. 15, 2003

(54) SALICYLIC ACID DERIVATIVES, PROCESSES FOR THEIR PREPARATION, COMPOSITIONS COMPRISING THEM, AND THEIR USE

(75) Inventors: Andreas Gypser, Mannheim (DE); Thomas Grote, Wachenheim (DE); Joachim Rheinheimer, Ludwigshafen (DE); Ingo Rose, Mannheim (DE); Oliver Cullmann, Heppenheim (DE); Markus Gewehr, Kastellaun (DE); Wassilios Grammenos, Ludwigshafen (DE); Jordi Tormo i Blasco, Limburgerhof (DE); Bernd Müller, Frankenthal (DE); Hubert Sauter, Mannheim (DE); Eberhard Ammermann, Heppenheim (DE); Siegfried Strathmann, Limburgerhof (DE); Gisela Lorenz, Hambach (DE); Reinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/896,971

(22) Filed: Jul. 2, 2001

(65) Prior Publication Data

US 2002/0032178 A1 Mar. 14, 2002

(30) Foreign Application Priority Data

Jul. 13, 2000 (DE) .......................... 100 34 180

(51) Int. Cl.[7] .......................... A01N 37/36; C07C 69/76; C07C 241/00
(52) U.S. Cl. .......................... 514/159; 560/34; 562/439; 564/186; 564/147; 564/202
(58) Field of Search .......................... 514/159; 560/34; 562/439; 564/186, 147, 202

(56) References Cited

U.S. PATENT DOCUMENTS 3,829,492 A   8/1974 Miller et al. ............. 260/566
6,001,879 A   12/1999 Seitz et al.

FOREIGN PATENT DOCUMENTS

DE    197 10609      9/1998
WO    WO 97/08135    3/1997
WO    99/27783       6/1999

OTHER PUBLICATIONS

El–Sabai et al, Egypt J. Pharm. 14 (1), pp. 67–73, 1979.*
El Sebai et al, Egypt J. Pharm.Sci. vol. 14, No. 1, (1973) pp 67–73.*
El_Sebai et al. "Synthesis of some new acid hydrazides structurally related to certain tuberculostatic agents" Egypt J. Pharm. Sci. vol. 14 No. 1, (1973) pp. 67–73.

* cited by examiner

Primary Examiner—Alan L. Rotman
Assistant Examiner—Hector M Reyes
(74) Attorney, Agent, or Firm—Keil & Weinkauf

(57) ABSTRACT

Salicylic acid derivatives of the formula I,

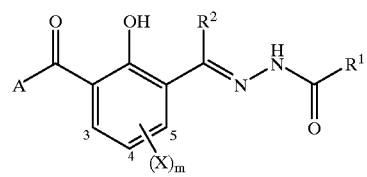

where the index and the substituents have the following meanings:

X is halogen, $NO_2$, cyano, alkyl or alkoxy;

m is 0, 1, 2 or 3, it being possible for the substituents X to be different from each other if n is greater than 1;

A is OH, alkoxy, $NH_2$, $NHCH_3$ or $N(CH_3)_2$;

$R^1$ is phenyl, naphthyl, cycloalkyl, 5-membered or 6-membered hetaryl or 5-membered or 6-membered heterocyclyl, comprising one to three N atoms and/or one O or S atom or one or two O and/or S atoms, the ring systems being unsubstituted or substituted;

$R^2$ is hydrogen, cyano, alkyl, alkenyl, alkynyl, haloalkyl, alkoxy or alkylthio, processes for the preparation of these compounds, compositions comprising them, and their use for controlling harmful fungi.

9 Claims, No Drawings

SALICYLIC ACID DERIVATIVES, PROCESSES FOR THEIR PREPARATION, COMPOSITIONS COMPRISING THEM, AND THEIR USE

The present invention relates to salicylic acid derivatives of the formula I

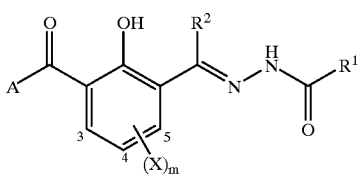

where the index and the substituents are as follows:

X is halogen, $NO_2$, cyano, $C_1$–$C_4$-alkyl or $C_1$–$C_4$-alkoxy;

m is 0, 1, 2 or 3, it being possible for the substituents X to differ from each other if n is greater than 1;

A is OH, $C_1$–$C_4$-alkoxy, $NH_2$, $NHCH_3$ or $N(CH_3)_2$;

$R^1$ is phenyl, naphthyl, $C_3$–$C_{10}$-cycloalkyl, 5-membered or 6-membered hetaryl or 5-membered or 6-membered heterocyclyl containing one to three N atoms and/or one O or S atom or one or two O and/or S atoms, the ring systems being unsubstituted or substituted by one to three radicals $R^a$:

$R^a$ is cyano, nitro, amino, aminocarbonyl, aminothiocarbonyl, halogen, hydroxyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, phenyl, phenoxy, benzyl, benzyloxy, 5- or 6-membered heterocyclyl, 5- or 6-membered hetaryl, 5- or 6-membered hetaryloxy, $C(=NOR^\alpha)$—$OR^\beta$ or $OC(R^\alpha)_2$—$C(R^\beta)$=$NOR^\beta$, the cyclic radicals, in turn, being unsubstituted or substituted by one to three radicals $R^b$:

$R^b$ is cyano, nitro, halogen, hydroxyl, amino, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkenyl, phenyl, phenoxy, phenylthio, benzyl, benzyloxy, 5- or 6-membered heterocyclyl, 5- or 6-membered hetaryl, 5- or 6-membered hetaryloxy or $C(=NOR^\alpha)$—$OR^\beta$;

$R^\alpha$, $R^\beta$ is hydrogen or $C_1$–$C_6$-alkyl;

$R^2$ is hydrogen, cyano, $C_1$–$C_6$-alkyl, $C_2$–$C_6$-alkenyl, $C_2$–$C_6$-alkynyl, $C_1$–$C_6$-haloalkyl, $C_1$–$C_6$-alkoxy or $C_1$–$C_6$-alkylthio, the hydrocarbon radicals being unsubstituted or partially or fully halogenated or it being possible for them to have attached to them one to three groups $R^c$:

$R^c$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_3$–$C_6$-alkenyloxy, $C_3$–$C_6$-alkynyloxy or $C_1$–$C_4$-alkylenedioxy which can be halogenated.

Furthermore, the invention relates to processes for the preparation of these compounds, to compositions comprising them, and to their use for controlling harmful fungi.

WO-A 97/08135, DE-A 197 10 609 and WO-A 99/27783 disclose acylaminosalicylamides for controlling harmful fungi.

However, their action is unsatisfactory in many cases.

It is an object of the invention to provide compounds with an improved action.

We have found that this object is achieved by the compounds defined at the outset. Moreover, there have been found processes for their preparation, compositions comprising them and methods of controlling phytopathogenic harmful fungi using the compounds I.

The compounds of the formula I differ from those of the prior art by the hydrazide group.

The compounds of the formula I show an increased efficacy against harmful fungi compared with the known compounds.

Compounds of the formula I can be prepared for example starting from alkyl salicylates of the formula II where A is $C_1$–$C_4$-alkoxy and Z is a protecting group which can be eliminated under acidic conditions, such as, for example, an acetyl group.

Compounds of the formula II can be obtained by free-radical halogenation under generally customary conditions, especially advantageously by bromination with N-bromosuccinimide (NBS) using azobisisobutyronitrile (AIBN) as free-radical initiator with exposure to light [cf. J. Amer. Chem. Soc., Vol. 71 (1949), p. 2137 et seq; ibid., Vol. 90 (1968), p. 1797 et seq]. Compounds of the formula II where A is methoxy, Z is acetyl and Hal is bromine are preferred.

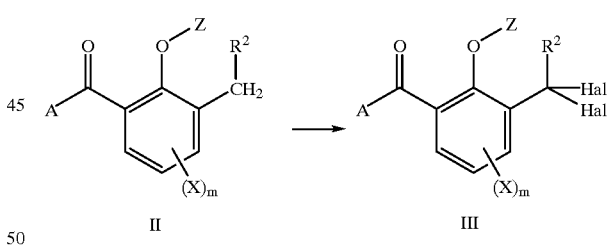

This reaction is usually carried out at temperatures of from 20° C. to 150° C., preferably from 50° C. to 100° C., in an inert organic solvent [cf. Can. J. Chem., Vol. 33 (1955), p. 1819; J. Org. Chem., Vol. 49 (1984), p. 2158].

Suitable solvents are halogenated hydrocarbons such as carbon tetrachloride, chloroform and chlorobenzene. Mixtures of the solvents mentioned may also be used.

In general, the starting materials are reacted with each other in equimolar amounts. It may be advantageous for the yield to employ NBS in an excess based on II.

The starting materials II required for the preparation of the compounds I are commercially available, known from the literature [Bull. Soc. Chim. Fr., Vol. 9 (1966), p. 2821; Biotechnol. Lett., Vol. 15 (1993), p. 469; J. Fluorine Chem., Vol. 74 (1995), p. 69] or can be prepared in accordance with the literature cited.

The dihalo compounds of the formula III are oxidized with elimination of the protecting group Z under acidic conditions to give the keto compounds IV.

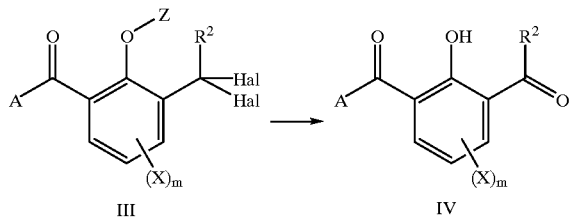

This reaction is usually carried out at temperatures of from 20° C. to 150° C., preferably from 20° C. to 100° C., in an inert organic solvent in the presence of an acid (cf. Org. Synth., Vol. 20 (1940), p. 92].

Suitable solvents are aliphatic hydrocarbons, aromatic hydrocarbons, halogenated hydrocarbons, ethers, alcohols such as methanol, ethanol, n-propanol, isopropanol, n-butanol and tert-butanol, and also dimethyl sulfoxide, N,N-dimethylformamide and N,N-dimethylacetamide, especially preferably methanol, ethanol and n-propanol. Mixtures of the solvents mentioned may also be used.

Acids and acidic catalysts which are used are inorganic acids such as hydrofluoric acid, aqueous hydrochloric acid, hydrobromic acid, sulfuric acid and perchloric acid, Lewis acids such as boron trifluoride, aluminum trichloride, iron (III) chloride, tin(IV) chloride, titanium(IV) chloride and zinc(II) chloride, and organic acids such as formic acid, acetic acid, propionic acid, oxalic acid, toluenesulfonic acid, benzenesulfonic acid, camphorsulfonic acid, citric acid and trifluoroacetic acid.

In general, the acids are employed in catalytic amounts, but they may also be used in equimolar amounts, in an excess or, if appropriate, as solvents.

To prepare compounds I where A is $NH_2$, $NHCH_3$ or $N(CH_3)_2$, salicylic esters IV are reacted with ammonia or methylamine to give salicylamides of the formula IV.1 where $R^3$ is hydrogen or methyl; the reaction with dimethylamine gives compounds of the formula IV.3:

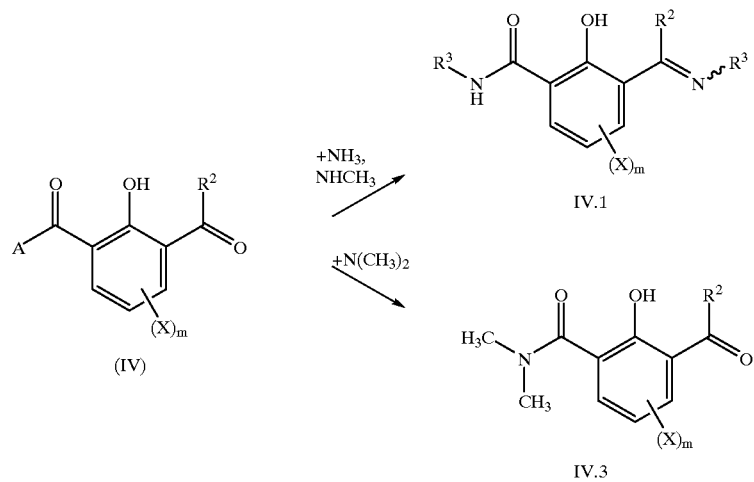

This reaction is usually carried out at temperatures of from 20° C. to 150° C., preferably from 20° C. to 100° C., in an inert organic solvent [cf. Arch. Pharm. (1982), p. 941].

Suitable solvents are aliphatic hydrocarbons, aromatic hydrocarbons, halogenated hydrocarbons, ethers such as diethyl ether, diisopropyl ether, tert-butyl methyl ether, dioxane, anisole and tetrahydrofuran, nitriles such as acetonitrile, alcohols, and dimethyl sulfoxide, N,N-dimethylformamide and N,N-dimethylacetamide, especially preferably N,N-dimethylformamide and N,N-dimethylacetamide. Mixtures of the solvents mentioned may also be used.

In general, the starting materials are reacted with each other in equimolar amounts. It may be advantageous for the yield to employ the amine in an excess based on IV.

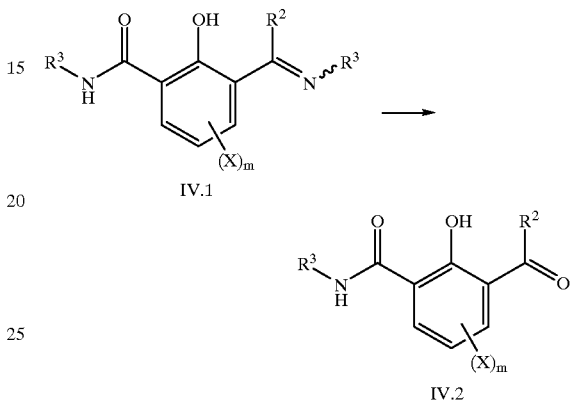

The imino group is usually eliminated from IV.1 at temperatures of from 20° C. to 150° C., preferably from 20° C. to 100° C., in an inert organic solvent in the presence of an acid [cf. J. Chem. Soc. (1957), p. 3807; J. Org. Chem., Vol. 6 (1941), p. 489].

Suitable solvents are aliphatic hydrocarbons, aromatic hydrocarbons, halogenated hydrocarbons, ethers, alcohols such as methanol, ethanol, n-propanol, isopropanol, n-butanol and tert-butanol, and dimethyl sulfoxide, N,N-dimethylformamide and N,N-dimethylacetamide, especially preferably methanol, ethanol and n-propanol. Mixtures of the solvents mentioned may also be used.

Acids and acidic catalysts which are used are inorganic acids such as hydrofluoric acid, aqueous hydrochloric acid, hydrobromic acid, sulfuric acid and perchloric acid, Lewis acids such as boron trifluoride, aluminum trichloride, iron (III) chloride, tin(IV) chloride, titanium(IV) chloride and zinc(II) chloride, and organic acids such as formic acid, acetic acid, propionic acid, oxalic acid, toluenesulfonic acid, benzenesulfonic acid, camphorsulfonic acid, citric acid and trifluoroacetic acid.

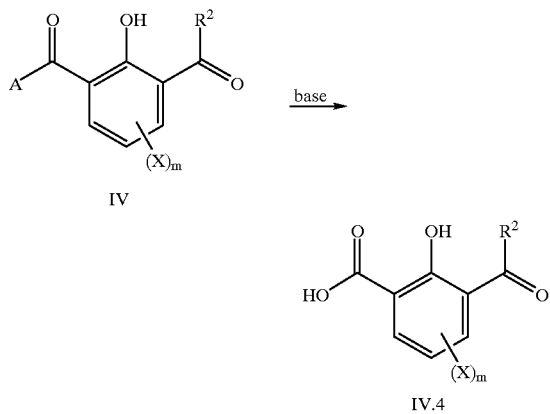

To prepare compounds of the formula I where A is hydroxyl, the alkyl esters of the formula IV are hydrolyzed by customary methods to give the salicylic acids of the formula IV.4 [cf. Organikum [Organic chemistry], 16th Ed., pp. 415 and 622, VEB Deutscher Verlag der Wissenschaften, Berlin 1985]. This reaction is usually carried out at temperatures of from 10° C. to 80° C., preferably 20° C. to 60° C., in an inert organic solvent in the presence of a base, such as alkali metal hydroxides or alkaline earth metal hydroxides, in particular sodium hydroxide or potassium hydroxide.

Depending on the form which radical A in formula I takes, compounds of the formulae IV, IV.2, IV.3 or IV.4 are reacted with hydrazides of the formula V to give compounds of the formula I.

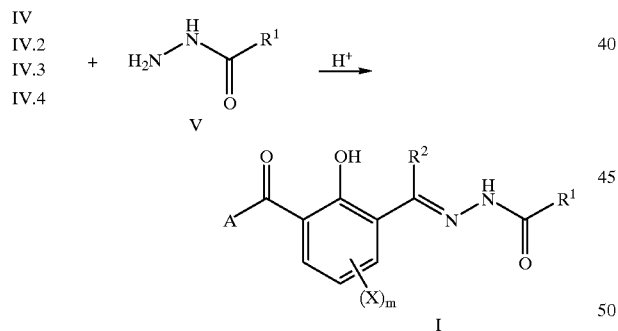

This reaction is usually carried out at temperatures of from 20° C. to 150° C., preferably from 20° C. to 80° C., in an inert organic solvent in the presence of an acid [cf. Org. Prep. Proced. Int., Vol. 30 (1998), p. 177; CH-A 661 276].

Suitable solvents are aliphatic hydrocarbons, aromatic hydrocarbons, halogenated hydrocarbons, ethers, nitrites, alcohols such as methanol, ethanol, n-propanol, isopropanol, n-butanol and tert-butanol, and dimethyl sulfoxide, N,N-dimethylformamide and N,N-dimethylacetamide, especially preferably methanol, ethanol, n-propanol, isopropanol or N,N-dimethylformamide. Mixtures of the solvents mentioned may also be used.

Acids and acidic catalysts which are used are inorganic acids such as hydrofluoric acid, aqueous hydrochloric acid, hydrobromic acid, sulfuric acid and perchloric acid, Lewis acids such as boron trifluoride, aluminum trichloride, iron (III) chloride, tin(IV) chloride, titanium(IV) chloride and zinc(II) chloride, and organic acids such as formic acid, acetic acid, propionic acid, oxalic acid, toluenesulfonic acid, benzenesulfonic acid, camphorsulfonic acid, citric acid and trifluoroacetic acid.

In general, the acids are employed in catalytic amounts, but they may also be used in equimolar amounts, in an excess or, if appropriate, as solvents.

In general, the starting materials are reacted with each other in equimolar amounts. It may be advantageous for the yield to employ V in an excess based on IV.

The reaction mixtures are worked up in the customary manner, for example by mixing with water, phase separation and, if appropriate, chromatographic purification of the crude products. Some of the intermediates and end products are obtained in the form of colorless or pale brown, viscous oils which are purified or freed from volatile components under reduced pressure and at a moderately elevated temperature. If the intermediates and end products are obtained as solids, they may also be purified by recrystallization or digestion.

If individual compounds I cannot be obtained by the above-described routes, they can be prepared by derivatizing the compounds I.

Upon their preparation, the compounds I may be obtained, owing to their C=C and C=N double bonds, as E/Z isomer mixtures which can be separated in the customary manner, for example by crystallization or chromatography, to give the individual compounds.

If, upon synthesis, isomer mixtures are obtained, separation is, however, not absolutely necessary since some of the individual isomers may be converted into each other during preparation for use, or upon use (for example with exposure to light, acids or bases). Similar conversions may also take place after use, for example in the treatment of plants in the treated plant or in the harmful fungus to be controlled.

In the definitions of the symbols in the above formulae, collective terms were used which generally represent the following substituents:

halogen: fluorine, chlorine, bromine and iodine;
alkyl: saturated, straight-chain or branched hydrocarbon radicals having 1 to 4 or 6 carbon atoms, for example $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2, 2-trimethylpropyl, 1-ethyl-1-methylpropyl and 1-ethyl-2-methylpropyl;
haloalkyl: straight-chain or branched alkyl groups having 1 to 6 carbon atoms (as mentioned above), it being possible for some or all of the hydrogen atoms in these groups to be replaced by halogen atoms as mentioned above, for example $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 6 carbon atoms (as mentioned above) which are bonded to the skeleton via an oxygen atom (—O—);

alkenyl: unsaturated, straight-chain or branched hydrocarbon radicals having 2 to 4 or 6 carbon atoms and one double bond in any position, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 4 or 6 carbon atoms and one triple bond in any position, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: monocyclic, saturated hydrocarbon groups having 3 to 6 carbon ring members such as cyclopropyl, cyclobutyl, cyclopentyl and cyclohexyl;

5- or 6-membered heterocyclyl contains, in addition to carbon ring members, one to three nitrogen atoms and/or one oxygen or sulfur atom or one or two oxygen and/or sulfur atoms, e.g. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-4-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

5-membered heteroaryl contains one to four nitrogen atoms or one to three nitrogen atoms and one sulfur or oxygen atom: 5-membered heteroaryl ring groups which may contain, in addition to carbon atoms, one to four nitrogen atoms or one to three nitrogen atoms and one sulfur or oxygen atom as ring members, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl contains one to three, or one to four, nitrogen atoms: 6-membered heteroaryl ring groups which, in addition to carbon atoms, may contain one to three, or one to four, nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

alkylene: divalent unbranched chains of 1 to 4 $CH_2$ groups, e.g. $CH_2$, $CH_2CH_2$, $CH_2CH_2CH_2$ and $CH_2CH_2CH_2CH_2$;

alkylenedioxy: divalent unbranched chains of 1 to 3 $CH_2$ groups, both valences being bonded to the skeleton by an oxygen atom, e.g. $OCH_2O$, $OCH_2CH_2O$ and $OCH_2CH_2CH_2O$.

Especially preferred with regard to the intended use of the salicylic acid derivatives of the formula I are the following meanings of the substituents, in each case alone or in combination:

Especially preferred are compounds of the formula I where A is methyl, methoxy, hydroxyl, amino and methylamino.

Particularly preferred are compounds IA:

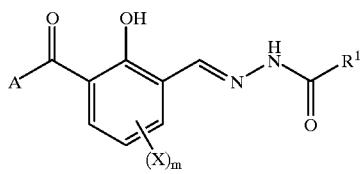

In addition, especially preferred compounds I are those where the index m is zero; these compounds are described by the formula IB:

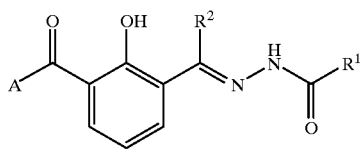

Especially preferred compounds I are furthermore those where $R^2$ is methyl.

Moreover, especially preferred compounds I are those where $(X)_m$ is in the para position relative to the phenol OH group and is halogen, $NO_2$, CN and $C_1$–$C_4$-alkoxy, in particular 4-chloro, 4-bromo and 4-$NO_2$.

Particularly preferred compounds I are also those where $R^1$ is cyclohexyl and phenyl which is unsubstituted or substituted by one to three radicals $R^a$, particularly phenyl. In the case of compounds where $R^1$ is cyclohexyl, the substituent $R^a$ may be in the E- or Z-position relative to the C—$R^1$ bond.

Especially preferred compounds I are those where $R^1$ is pyrazole, pyrimidine, pyridine, pyrazine and thiophene, each of which is unsubstituted or substituted by one to three radicals $R^a$.

Also preferred are compounds I where $R^a$ is chlorine, bromine, nitro, cyano, methyl, ethyl, n- and iso-propyl, n- and sec- and tert-butyl and phenyl, the aromatic ring being unsubstituted or substituted by one or two radicals from the group consisting of chlorine, bromine, nitro, cyano and methyl.

Equally especially preferred are compounds I where $R^2$ is hydrogen, methyl, methoxy and cyano, in particular hydrogen and methyl.

The especially preferred embodiments of the intermediates with regard to the variables correspond to those of radicals A, $(X)_m$, $R^1$ and $R^2$ of the formula I.

Particularly preferred with regard to their use are the compounds I which are compiled in the tables which follow. In addition, the groups mentioned in the tables for a substituent constitute an especially preferred embodiment of the substituent in question, independently of the combination in which they are mentioned.

Table 1
Compounds of the formula I where m is zero, A is methoxy and $R^2$ is hydrogen, and the radical $R^1$ for each compound corresponds to one line of Table A

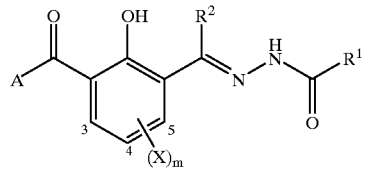

Table 2
Compounds of the formula I where m is zero, A is methoxy and $R^2$ is methyl, and the radical $R^1$ for each compound corresponds to one line of Table A Table 3
Compounds of the formula I where m is zero, A is methoxy and $R^2$ is methoxy, and the radical $R^1$ for each compound corresponds to one line of Table A Table 4
Compounds of the formula I where m is zero, A is methoxy and $R^2$ is cyano, and the radical $R^1$ for each compound corresponds to one line of Table A Table 5
Compounds of the formula I where $(X)_m$ is 3-chloro, A is methoxy and $R^2$ is hydrogen, and the radical $R^1$ for each compound corresponds to one line of Table A Table 6
Compounds of the formula I where $(X)_m$ is 3-chloro, A is methoxy and $R^2$ is methyl, and the radical $R^1$ for each compound corresponds to one line of Table A Table 7
Compounds of the formula I where $(X)_m$ is 3-chloro, A is methoxy and $R^2$ is methoxy, and the radical $R^1$ for each compound corresponds to one line of Table A Table 8
Compounds of the formula I where $(X)_m$ is 3-chloro, A is methoxy and $R^2$ is cyano, and the radical $R^1$ for each compound corresponds to one line of Table A Table 9
Compounds of the formula I where $(X)_m$ is 4-chloro, A is methoxy and $R^2$ is hydrogen, and the radical $R^1$ for each compound corresponds to one line of Table A Table 10
Compounds of the formula I where $(X)_m$ is 4-chloro, A is methoxy and $R^2$ is methyl, and the radical $R^1$ for each compound corresponds to one line of Table A Table 11
Compounds of the formula I where $(X)_m$ is 4-chloro, A is methoxy and $R^2$ is methoxy, and the radical $R^1$ for each compound corresponds to one line of Table A Table 12
Compounds of the formula I where $(X)_m$ is 4-chloro, A is methoxy and $R^2$ is cyano, and the radical $R^1$ for each compound corresponds to one line of Table A Table 13
Compounds of the formula I where $(X)_m$ is 5-chloro, A is methoxy and $R^2$ is hydrogen, and the radical $R^1$ for each compound corresponds to one line of Table A Table 14
Compounds of the formula I where $(X)_m$ is 5-chloro, A is methoxy and $R^2$ is methyl, and the radical $R^1$ for each compound corresponds to one line of Table A Table 15
Compounds of the formula I where $(X)_m$ is 5-chloro, A is methoxy and $R^2$ is methoxy, and the radical $R^1$ for each compound corresponds to one line of Table A Table 16
Compounds of the formula I where $(X)_m$ is 5-chloro, A is methoxy and $R^2$ is cyano, and the radical $R^1$ for each compound corresponds to one line of Table A Table 17
Compounds of the formula I where $(X)_m$ is 3-bromo, A is methoxy and $R^2$ is hydrogen, and the radical $R^1$ for each compound corresponds to one line of Table A Table 18
Compounds of the formula I where $(X)_m$ is 3-bromo, A is methoxy and $R^2$ is methyl, and the radical $R^1$ for each compound corresponds to one line of Table A Table 19
Compounds of the formula I where $(X)_m$ is 3-bromo, A is methoxy and $R^2$ is methoxy, and the radical $R^1$ for each compound corresponds to one line of Table A Table 20
Compounds of the formula I where $(X)_m$ is 3-bromo, A is methoxy and $R^2$ is cyano, and the radical $R^1$ for each compound corresponds to one line of Table A Table 21
Compounds of the formula I where $(X)_m$ is 4-bromo, A is methoxy and $R^2$ is hydrogen, and the radical $R^1$ for each compound corresponds to one line of Table A Table 22
Compounds of the formula I where $(X)_m$ is 4-bromo, A is methoxy and $R^2$ is methyl, and the radical $R^1$ for each compound corresponds to one line of Table A Table 23
Compounds of the formula I where $(X)_m$ is 4-bromo, A is methoxy and $R^2$ is methoxy, and the radical $R^1$ for each compound corresponds to one line of Table A Table 24
Compounds of the formula I where $(X)_m$ is 4-bromo, A is methoxy and $R^2$ is cyano, and the radical $R^1$ for each compound corresponds to one line of Table A Table 25
Compounds of the formula I where $(X)_m$ is 5-bromo, A is methoxy and $R^2$ is hydrogen, and the radical $R^1$ for each compound corresponds to one line of Table A Table 26
Compounds of the formula I where $(X)_m$ is 5-bromo, A is methoxy and $R^2$ is methyl, and the radical $R^1$ for each compound corresponds to one line of Table A Table 27
Compounds of the formula I where $(X)_m$ is 5-bromo, A is methoxy and $R^2$ is methoxy, and the radical $R^1$ for each compound corresponds to one line of Table A Table 28
Compounds of the formula I where $(X)_m$ is 5-bromo, A is methoxy and $R^2$ is cyano, and the radical $R^1$ for each compound corresponds to one line of Table A Table 29
Compounds of the formula I where $(X)_m$ is 3-nitro, A is methoxy and $R^2$ is hydrogen, and the radical $R^1$ for each compound corresponds to one line of Table A Table 30
Compounds of the formula I where $(X)_m$ is 3-nitro, A is methoxy and $R^2$ is methyl, and the radical $R^1$ for each compound corresponds to one line of Table A Table 31
Compounds of the formula I where $(X)_m$ is 3-nitro, A is methoxy and $R^2$ is methoxy, and the radical $R^1$ for each compound corresponds to one line of Table A Table 32
Compounds of the formula I where $(X)_m$ is 3-nitro, A is methoxy and $R^2$ is cyano, and the radical $R^1$ for each compound corresponds to one line of Table A Table 33
Compounds of the formula I where $(X)_m$ is 4-nitro, A is methoxy and $R^2$ is hydrogen, and the radical $R^1$ for each compound corresponds to one line of Table A Table 34
Compounds of the formula I where $(X)_m$ is 4-nitro, A is methoxy and $R^2$ is methyl, and the radical $R^1$ for each compound corresponds to one line of Table A Table 35
Compounds of the formula I where $(X)_m$ is 4-nitro, A is methoxy and $R^2$ is methoxy, and the radical $R^1$ for each compound corresponds to one line of Table A Table 36
Compounds of the formula I where $(X)_m$ is 4-nitro, A is methoxy and $R^2$ is cyano, and the radical $R^1$ for each compound corresponds to one line of Table A Table 37
Compounds of the formula I where $(X)_m$ is 5-nitro, A is methoxy and $R^2$ is hydrogen, and the radical $R^1$ for each compound corresponds to one line of Table A Table 38
Compounds of the formula I where $(X)_m$ is 5-nitro, A is methoxy and $R^2$ is methyl, and the radical $R^1$ for each compound corresponds to one line of Table A Table 39
Compounds of the formula I where $(X)_m$ is 5-nitro, A is methoxy and $R^2$ is methoxy, and the radical $R^1$ for each compound corresponds to one line of Table A Table 40
Compounds of the formula I where $(X)_m$ is 5-nitro, A is methoxy and $R^2$ is cyano, and the radical $R^1$ for each compound corresponds to one line of Table A Table 41
Compounds of the formula I where m is zero, A is amino and $R^2$ is hydrogen, and the radical $R^1$ for each compound corresponds to one line of Table A Table 42
Compounds of the formula I where m is zero, A is amino and $R^2$ is methyl, and the radical $R^1$ for each compound corresponds to one line of Table A Table 43
Compounds of the formula I where m is zero, A is amino and $R^2$ is methoxy, and the radical $R^1$ for each compound corresponds to one line of Table A Table 44
Compounds of the formula I where m is zero, A is amino and $R^2$ is cyano, and the radical $R^1$ for each compound corresponds to one line of Table A Table 45
Compounds of the formula I where $(X)_m$ is 3-chloro, A is amino and $R^2$ is hydrogen, and the radical $R^1$ for each compound corresponds to one line of Table A Table 46
Compounds of the formula I where $(X)_m$ is 3-chloro, A is amino and $R^2$ is methyl, and the radical $R^1$ for each compound corresponds to one line of Table A Table 47
Compounds of the formula I where $(X)_m$ is 3-chloro, A is amino and $R^2$ is methoxy, and the radical $R^1$ for each compound corresponds to one line of Table A Table 48
Compounds of the formula I where $(X)_m$ is 3-chloro, A is amino and $R^2$ is cyano, and the radical $R^1$ for each compound corresponds to one line of Table A Table 49
Compounds of the formula I where $(X)_m$ is 4-chloro, A is amino and $R^2$ is hydrogen, and the radical $R^1$ for each compound corresponds to one line of Table A Table 50
Compounds of the formula I where $(X)_m$ is 4-chloro, A is amino and $R^2$ is methyl, and the radical $R^1$ for each compound corresponds to one line of Table A Table 51
Compounds of the formula I where $(X)_m$ is 4-chloro, A is amino and $R^2$ is methoxy, and the radical $R^1$ for each compound corresponds to one line of Table A Table 52
Compounds of the formula I where $(X)_m$ is 4-chloro, A is amino and $R^2$ is cyano, and the radical $R^1$ for each compound corresponds to one line of Table A Table 53
Compounds of the formula I where $(X)_m$ is 5-chloro, A is amino and $R^2$ is hydrogen, and the radical $R^1$ for each compound corresponds to one line of Table A Table 54
Compounds of the formula I where $(X)_m$ is 5-chloro, A is amino and $R^2$ is methyl, and the radical $R^1$ for each compound corresponds to one line of Table A Table 55
Compounds of the formula I where $(X)_m$ is 5-chloro, A is amino and $R^2$ is methoxy, and the radical $R^1$ for each compound corresponds to one line of Table A Table 56
Compounds of the formula I where $(X)_m$ is 5-chloro, A is amino and $R^2$ is cyano, and the radical $R^1$ for each compound corresponds to one line of Table A Table 57
Compounds of the formula I where $(X)_m$ is 3-bromo, A is amino and $R^2$ is hydrogen, and the radical $R^1$ for each compound corresponds to one line of Table A Table 58
Compounds of the formula I where $(X)_m$ is 3-bromo, A is amino and $R^2$ is methyl, and the radical $R^1$ for each compound corresponds to one line of Table A Table 59
Compounds of the formula I where $(X)_m$ is 3-bromo, A is amino and $R^2$ is methoxy, and the radical $R^1$ for each compound corresponds to one line of Table A Table 60
Compounds of the formula I where $(X)_m$ is 3-bromo, A is amino and $R^2$ is cyano, and the radical $R^1$ for each compound corresponds to one line of Table A Table 61
Compounds of the formula I where $(X)_m$ is 4-bromo, A is amino and $R^2$ is hydrogen, and the radical $R^1$ for each compound corresponds to one line of Table A Table 62
Compounds of the formula I where $(X)_m$ is 4-bromo, A is amino and $R^2$ is methyl, and the radical $R^1$ for each compound corresponds to one line of Table A Table 63
Compounds of the formula I where $(X)_m$ is 4-bromo, A is amino and $R^2$ is methoxy, and the radical $R^1$ for each compound corresponds to one line of Table A Table 64
Compounds of the formula I where $(X)_m$ is 4-bromo, A is amino and $R^2$ is isopropyl, and the radical $R^1$ for each compound corresponds to one line of Table A Table 65
Compounds of the formula I where $(X)_m$ is 5-bromo, A is amino and $R^2$ is hydrogen, and the radical $R^1$ for each compound corresponds to one line of Table A Table 66
Compounds of the formula I where $(X)_m$ is 5-bromo, A is amino and $R^2$ is methyl, and the radical $R^1$ for each compound corresponds to one line of Table A Table 67
Compounds of the formula I where $(X)_m$ is 5-bromo, A is amino and $R^2$ is methoxy, and the radical $R^1$ for each compound corresponds to one line of Table A Table 68
Compounds of the formula I where $(X)_m$ is 5-bromo, A is amino and $R^2$ is cyano, and the radical $R^1$ for each compound corresponds to one line of Table A Table 69
Compounds of the formula I where $(X)_m$ is 3-nitro, A is amino and $R^2$ is hydrogen, and the radical $R^1$ for each compound corresponds to one line of Table A Table 70
Compounds of the formula I where $(X)_m$ is 3-nitro, A is amino and $R^2$ is methyl, and the radical $R^1$ for each compound corresponds to one line of Table A Table 71
Compounds of the formula I where $(X)_m$ is 3-nitro, A is amino and $R^2$ is methoxy, and the radical $R^1$ for each compound corresponds to one line of Table A Table 72
Compounds of the formula I where $(X)_m$ is 3-nitro, A is amino and $R^2$ is cyano, and the radical $R^1$ for each compound corresponds to one line of Table A Table 73
Compounds of the formula I where $(X)_m$ is 4-nitro, A is amino and $R^2$ is hydrogen, and the radical $R^1$ for each compound corresponds to one line of Table A Table 74
Compounds of the formula I where $(X)_m$ is 4-nitro, A is amino and $R^2$ is methyl, and the radical $R^1$ for each compound corresponds to one line of Table A Table 75
Compounds of the formula I where $(X)_m$ is 4-nitro, A is amino and $R^2$ is methoxy, and the radical $R^1$ for each compound corresponds to one line of Table A Table 76
Compounds of the formula I where $(X)_m$ is 4-nitro, A is amino and $R^2$ is cyano, and the radical $R^1$ for each compound corresponds to one line of Table A Table 77
Compounds of the formula I where $(X)_m$ is 5-nitro, A is amino and $R^2$ is hydrogen, and the radical $R^1$ for each compound corresponds to one line of Table A Table 78
Compounds of the formula I where $(X)_m$ is 5-nitro, A is amino and $R^2$ is methyl, and the radical $R^1$ for each compound corresponds to one line of Table A Table 79
Compounds of the formula I where $(X)_m$ is 5-nitro, A is amino and $R^2$ is methoxy, and the radical $R^1$ for each compound corresponds to one line of Table A Table 80
Compounds of the formula I where $(X)_m$ is 5-nitro, A is amino and $R^2$ is cyano, and the radical $R^1$ for each compound corresponds to one line of Table A Table 81
Compounds of the formula I where m is zero, A is methylamino and $R^2$ is hydrogen, and the radical $R^1$ for each compound corresponds to one line of Table A Table 82
Compounds of the formula I where m is zero, A is methylamino and $R^2$ is methyl, and the radical $R^1$ for each compound corresponds to one line of Table A Table 83
Compounds of the formula I where m is zero, A is methylamino and $R^2$ is methoxy, and the radical $R^1$ for each compound corresponds to one line of Table A Table 84
Compounds of the formula I where m is zero, A is methylamino and $R^2$ is cyano, and the radical $R^1$ for each compound corresponds to one line of Table A Table 85
Compounds of the formula I where $(X)_m$ is 3-chloro, A is methylamino and $R^2$ is hydrogen, and the radical $R^1$ for each compound corresponds to one line of Table A Table 86
Compounds of the formula I where $(X)_m$ is 3-chloro, A is methylamino and $R^2$ is methyl, and the radical $R^1$ for each compound corresponds to one line of Table A Table 87
Compounds of the formula I where $(X)_m$ is 3-chloro, A is methylamino and $R^2$ is methoxy, and the radical $R^1$ for each compound corresponds to one line of Table A Table 88
Compounds of the formula I where $(X)_m$ is 3-chloro, A is methylamino and $R^2$ is cyano, and the radical $R^1$ for each compound corresponds to one line of Table A Table 89
Compounds of the formula I where $(X)_m$ is 4-chloro, A is methylamino and $R^2$ is hydrogen, and the radical $R^1$ for each compound corresponds to one line of Table A Table 90
Compounds of the formula I where $(X)_m$ is 4-chloro, A is methylamino and $R^2$ is methyl, and the radical $R^1$ for each compound corresponds to one line of Table A Table 91
Compounds of the formula I where $(X)_m$ is 4-chloro, A is methylamino and $R^2$ is methoxy, and the radical $R^1$ for each compound corresponds to one line of Table A Table 92
Compounds of the formula I where $(X)_m$ is 4-chloro, A is methylamino and $R^2$ is cyano, and the radical $R^1$ for each compound corresponds to one line of Table A Table 93
Compounds of the formula I where $(X)_m$ is 5-chloro, A is methylamino and $R^2$ is hydrogen, and the radical $R^1$ for each compound corresponds to one line of Table A Table 94
Compounds of the formula I where $(X)_m$ is 5-chloro, A is methylamino and $R^2$ is methyl, and the radical $R^1$ for each compound corresponds to one line of Table A Table 95
Compounds of the formula I where $(X)_m$ is 5-chloro, A is methylamino and $R^2$ is methoxy, and the radical $R^1$ for each compound corresponds to one line of Table A Table 96
Compounds of the formula I where $(X)_m$ is 5-chloro, A is methylamino and $R^2$ is cyano, and the radical $R^1$ for each compound corresponds to one line of Table A Table 97
Compounds of the formula I where $(X)_m$ is 3-bromo, A is methylamino and $R^2$ is hydrogen, and the radical $R^1$ for each compound corresponds to one line of Table A Table 98
Compounds of the formula I where $(X)_m$ is 3-bromo, A is methylamino and $R^2$ is methyl, and the radical $R^1$ for each compound corresponds to one line of Table A Table 99
Compounds of the formula I where $(X)_m$ is 3-bromo, A is methylamino and $R^2$ is methoxy, and the radical $R^1$ for each compound corresponds to one line of Table A Table 100
Compounds of the formula I where $(X)_m$ is 3-bromo, A is methylamino and $R^2$ is cyano, and the radical $R^1$ for each compound corresponds to one line of Table A Table 101
Compounds of the formula I where $(X)_m$ is 4-bromo, A is methylamino and $R^2$ is hydrogen, and the radical $R^1$ for each compound corresponds to one line of Table A Table 102
Compounds of the formula I where $(X)_m$ is 4-bromo, A is methylamino and $R^2$ is methyl, and the radical $R^1$ for each compound corresponds to one line of Table A Table 103
Compounds of the formula I where $(X)_m$ is 4-bromo, A is methylamino and $R^2$ is methoxy, and the radical $R^1$ for each compound corresponds to one line of Table A Table 104
Compounds of the formula I where $(X)_m$ is 4-bromo, A is methylamino and $R^2$ is cyano, and the radical $R^1$ for each compound corresponds to one line of Table A Table 105
Compounds of the formula I where $(X)_m$ is 5-bromo, A is methylamino and $R^2$ is hydrogen, and the radical $R^1$ for each compound corresponds to one line of Table A Table 106
Compounds of the formula I where $(X)_m$ is 5-bromo, A is methylamino and $R^2$ is methyl, and the radical $R^1$ for each compound corresponds to one line of Table A Table 107
Compounds of the formula I where $(X)_m$ is 5-bromo, A is methylamino and $R^2$ is methoxy, and the radical $R^1$ for each compound corresponds to one line of Table A Table 108
Compounds of the formula I where $(X)_m$ is 5-bromo, A is methylamino and $R^2$ is cyano, and the radical $R^1$ for each compound corresponds to one line of Table A Table 109
Compounds of the formula I where $(X)_m$ is 3-nitro, A is methylamino and $R^2$ is hydrogen, and the radical $R^1$ for each compound corresponds to one line of Table A Table 110
Compounds of the formula I where $(X)_m$ is 3-nitro, A is methylamino and $R^2$ is methyl, and the radical $R^1$ for each compound corresponds to one line of Table A Table 111
Compounds of the formula I where $(X)_m$ is 3-nitro, A is methylamino and $R^2$ is methoxy, and the radical $R^1$ for each compound corresponds to one line of Table A Table 112
Compounds of the formula I where $(X)_m$ is 3-nitro, A is methylamino and $R^2$ is cyano, and the radical $R^1$ for each compound corresponds to one line of Table A Table 113
Compounds of the formula I where $(X)_m$ is 4-nitro, A is methylamino and $R^2$ is hydrogen, and the radical $R^1$ for each compound corresponds to one line of Table A Table 114
Compounds of the formula I where $(X)_m$ is 4-nitro, A is methylamino and $R^2$ is methyl, and the radical $R^1$ for each compound corresponds to one line of Table A Table 115
Compounds of the formula I where $(X)_m$ is 4-nitro, A is methylamino and $R^2$ is methoxy, and the radical $R^1$ for each compound corresponds to one line of Table A Table 116
Compounds of the formula I where $(X)_m$ is 4-nitro, A is methylamino and $R^2$ is cyano, and the radical $R^1$ for each compound corresponds to one line of Table A Table 117
Compounds of the formula I where $(X)_m$ is 5-nitro, A is methylamino and $R^2$ is hydrogen, and the radical $R^1$ for each compound corresponds to one line of Table A Table 118
Compounds of the formula I where $(X)_m$ is 5-nitro, A is methylamino and $R^2$ is methyl, and the radical $R^1$ for each compound corresponds to one line of Table A Table 119
Compounds of the formula I where $(X)_m$ is 5-nitro, A is methylamino and $R^2$ is methoxy, and the radical $R^1$ for each compound corresponds to one line of Table A Table 120
Compounds of the formula I where $(X)_m$ is 5-nitro, A is methylamino and $R^2$ is cyano, and the radical $R^1$ for each compound corresponds to one line of Table A Table 121
Compounds of the formula I where m is zero, A is dimethylamino and $R^2$ is hydrogen, and the radical $R^1$ for each compound corresponds to one line of Table A Table 122
Compounds of the formula I where m is zero, A is dimethylamino and $R^2$ is methyl, and the radical $R^1$ for each compound corresponds to one line of Table A Table 123
Compounds of the formula I where m is zero, A is dimethylamino and $R^2$ is methoxy, and the radical $R^1$ for each compound corresponds to one line of Table A Table 124
Compounds of the formula I where m is zero, A is dimethylamino and $R^2$ is cyano, and the radical $R^1$ for each compound corresponds to one line of Table A Table 125
Compounds of the formula I where $(X)_m$ is 3-chloro, A is dimethylamino and $R^2$ is hydrogen, and the radical $R^1$ for each compound corresponds to one line of Table A Table 126
Compounds of the formula I where $(X)_m$ is 3-chloro, A is dimethylamino and $R^2$ is methyl, and the radical $R^1$ for each compound corresponds to one line of Table A Table 127
Compounds of the formula I where $(X)_m$ is 3-chloro, A is dimethylamino and $R^2$ is methoxy, and the radical $R^1$ for each compound corresponds to one line of Table A Table 128
Compounds of the formula I where $(X)_m$ is 3-chloro, A is dimethylamino and $R^2$ is cyano, and the radical $R^1$ for each compound corresponds to one line of Table A Table 129
Compounds of the formula I where $(X)_m$ is 4-chloro, A is dimethylamino and $R^2$ is hydrogen, and the radical $R^1$ for each compound corresponds to one line of Table A Table 130
Compounds of the formula I where $(X)_m$ is 4-chloro, A is dimethylamino and $R^2$ is methyl, and the radical $R^1$ for each compound corresponds to one line of Table A Table 131
Compounds of the formula I where $(X)_m$ is 4-chloro, A is dimethylamino and $R^2$ is methoxy, and the radical $R^1$ for each compound corresponds to one line of Table A Table 132
Compounds of the formula I where $(X)_m$ is 4-chloro, A is dimethylamino and $R^2$ is cyano, and the radical $R^1$ for each compound corresponds to one line of Table A Table 133
Compounds of the formula I where $(X)_m$ is 5-chloro, A is dimethylamino and $R^2$ is hydrogen, and the radical $R^1$ for each compound corresponds to one line of Table A Table 134
Compounds of the formula I where $(X)_m$ is 5-chloro, A is dimethylamino and $R^2$ is methyl, and the radical $R^1$ for each compound corresponds to one line of Table A Table 135
Compounds of the formula I where $(X)_m$ is 5-chloro, A is dimethylamino and $R^2$ is methoxy, and the radical $R^1$ for each compound corresponds to one line of Table A Table 136
Compounds of the formula I where $(X)_m$ is 5-chloro, A is dimethylamino and $R^2$ is cyano, and the radical $R^1$ for each compound corresponds to one line of Table A Table 137
Compounds of the formula I where $(X)_m$ is 3-bromo, A is dimethylamino and $R^2$ is hydrogen, and the radical $R^1$ for each compound corresponds to one line of Table A Table 138
Compounds of the formula I where $(X)_m$ is 3-bromo, A is dimethylamino and $R^2$ is methyl, and the radical $R^1$ for each compound corresponds to one line of Table A Table 139
Compounds of the formula I where $(X)_m$ is 3-bromo, A is dimethylamino and $R^2$ is methoxy, and the radical $R^1$ for each compound corresponds to one line of Table A Table 140
Compounds of the formula I where $(X)_m$ is 3-bromo, A is dimethylamino and $R^2$ is cyano, and the radical $R^1$ for each compound corresponds to one line of Table A Table 141
Compounds of the formula I where $(X)_m$ is 4-bromo, A is dimethylamino and $R^2$ is hydrogen, and the radical $R^1$ for each compound corresponds to one line of Table A Table 142
Compounds of the formula I where $(X)_m$ is 4-bromo, A is dimethylamino and $R^2$ is methyl, and the radical $R^1$ for each compound corresponds to one line of Table A Table 143
Compounds of the formula I where $(X)_m$ is 4-bromo, A is dimethylamino and $R^2$ is methoxy, and the radical $R^1$ for each compound corresponds to one line of Table A Table 144
Compounds of the formula I where $(X)_m$ is 4-bromo, A is dimethylamino and $R^2$ is cyano, and the radical $R^1$ for each compound corresponds to one line of Table A Table 145
Compounds of the formula I where $(X)_m$ is 5-bromo, A is dimethylamino and $R^2$ is hydrogen, and the radical $R^1$ for each compound corresponds to one line of Table A Table 146
Compounds of the formula I where $(X)_m$ is 5-bromo, A is dimethylamino and $R^2$ is methyl, and the radical $R^1$ for each compound corresponds to one line of Table A Table 147
Compounds of the formula I where $(X)_m$ is 5-bromo, A is dimethylamino and $R^2$ is methoxy, and the radical $R^1$ for each compound corresponds to one line of Table A Table 148
Compounds of the formula I where $(X)_m$ is 5-bromo, A is dimethylamino and $R^2$ is cyano, and the radical $R^1$ for each compound corresponds to one line of Table A Table 149
Compounds of the formula I where $(X)_m$ is 3-nitro, A is dimethylamino and $R^2$ is hydrogen, and the radical $R^1$ for each compound corresponds to one line of Table A Table 150
Compounds of the formula I where $(X)_m$ is 3-nitro, A is dimethylamino and $R^2$ is methyl, and the radical $R^1$ for each compound corresponds to one line of Table A Table 151
Compounds of the formula I where $(X)_m$ is 3-nitro, A is dimethylamino and $R^2$ is methoxy, and the radical $R^1$ for each compound corresponds to one line of Table A Table 152
Compounds of the formula I where $(X)_m$ is 3-nitro, A is dimethylamino and $R^2$ is cyano, and the radical $R^1$ for each compound corresponds to one line of Table A Table 153
Compounds of the formula I where $(X)_m$ is 4-nitro, A and $R^2$ are hydrogen, and the radical $R^1$ for each compound corresponds to one line of Table A Table 154
Compounds of the formula I where $(X)_m$ is 4-nitro, A is dimethylamino and $R^2$ is methyl, and the radical $R^1$ for each compound corresponds to one line of Table A Table 155
Compounds of the formula I where $(X)_m$ is 4-nitro, A is dimethylamino and $R^2$ is methoxy, and the radical $R^1$ for each compound corresponds to one line of Table A Table 156
Compounds of the formula I where $(X)_m$ is 4-nitro, A is dimethylamino and $R^2$ is cyano, and the radical $R^1$ for each compound corresponds to one line of Table A Table 157
Compounds of the formula I where $(X)_m$ is 5-nitro, A is dimethylamino and $R^2$ is hydrogen, and the radical $R^1$ for each compound corresponds to one line of Table A Table 158
Compounds of the formula I where $(X)_m$ is 5-nitro, A is dimethylamino and $R^2$ is methyl, and the radical $R^1$ for each compound corresponds to one line of Table A Table 159
Compounds of the formula I where $(X)_m$ is 5-nitro, A is dimethylamino and $R^2$ is methoxy, and the radical $R^1$ for each compound corresponds to one line of Table A Table 160
Compounds of the formula I where $(X)_m$ is 5-nitro, A is dimethylamino and $R^2$ is cyano, and the radical $R^1$ for each compound corresponds to one line of Table A Table 161
Compounds of the formula I where m is zero, A is hydroxyl and $R^2$ is hydrogen, and the radical $R^1$ for each compound corresponds to one line of Table A Table 162
Compounds of the formula I where m is zero, A is hydroxyl and $R^2$ is methyl, and the radical $R^1$ for each compound corresponds to one line of Table A Table 163
Compounds of the formula I where m is zero, A is hydroxyl and $R^2$ is methoxy, and the radical $R^1$ for each compound corresponds to one line of Table A Table 164
Compounds of the formula I where m is zero, A is hydroxyl and $R^2$ is cyano, and the radical $R^1$ for each compound corresponds to one line of Table A Table 165
Compounds of the formula I where $(X)_m$ is 3-chloro, A is hydroxyl and $R^2$ is hydrogen, and the radical $R^1$ for each compound corresponds to one line of Table A Table 166
Compounds of the formula I where $(X)_m$ is 3-chloro, A is hydroxyl and $R^2$ is methyl, and the radical $R^1$ for each compound corresponds to one line of Table A Table 167
Compounds of the formula I where $(X)_m$ is 3-chloro, A is hydroxyl and $R^2$ is methoxy, and the radical $R^1$ for each compound corresponds to one line of Table A Table 168
Compounds of the formula I where $(X)_m$ is 3-chloro, A is hydroxyl and $R^2$ is cyano, and the radical $R^1$ for each compound corresponds to one line of Table A Table 169
Compounds of the formula I where $(X)_m$ is 4-chloro, A is hydroxyl and $R^2$ is hydrogen, and the radical $R^1$ for each compound corresponds to one line of Table A Table 170
Compounds of the formula I where $(X)_m$ is 4-chloro, A is hydroxyl and $R^2$ is methyl, and the radical $R^1$ for each compound corresponds to one line of Table A Table 171
Compounds of the formula I where $(X)_m$ is 4-chloro, A is hydroxyl and $R^2$ is methoxy, and the radical $R^1$ for each compound corresponds to one line of Table A Table 172
Compounds of the formula I where $(X)_m$ is 4-chloro, A is hydroxyl and $R^2$ is cyano, and the radical $R^1$ for each compound corresponds to one line of Table A Table 173
Compounds of the formula I where $(X)_m$ is 5-chloro, A is hydroxyl and $R^2$ is hydrogen, and the radical $R^1$ for each compound corresponds to one line of Table A Table 174
Compounds of the formula I where $(X)_m$ is 5-chloro, A is hydroxyl and $R^2$ is methyl, and the radical $R^1$ for each compound corresponds to one line of Table A Table 175
Compounds of the formula I where $(X)_m$ is 5-chloro, A is hydroxyl and $R^2$ is methoxy, and the radical $R^1$ for each compound corresponds to one line of Table A Table 176
Compounds of the formula I where $(X)_m$ is 5-chloro, A is hydroxyl and $R^2$ is cyano, and the radical $R^1$ for each compound corresponds to one line of Table A Table 177
Compounds of the formula I where $(X)_m$ is 3-bromo, A is hydroxyl and $R^2$ is hydrogen, and the radical $R^1$ for each compound corresponds to one line of Table A Table 178
Compounds of the formula I where $(X)_m$ is 3-bromo, A is hydroxyl and $R^2$ is methyl, and the radical $R^1$ for each compound corresponds to one line of Table A Table 179
Compounds of the formula I where $(X)_m$ is 3-bromo, A is hydroxyl and $R^2$ is methoxy, and the radical $R^1$ for each compound corresponds to one line of Table A Table 180
Compounds of the formula I where $(X)_m$ is 3-bromo, A is hydroxyl and $R^2$ is cyano, and the radical $R^1$ for each compound corresponds to one line of Table A Table 181
Compounds of the formula I where $(X)_m$ is 4-bromo, A is hydroxyl and $R^2$ is hydrogen, and the radical $R^1$ for each compound corresponds to one line of Table A Table 182
Compounds of the formula I where $(X)_m$ is 4-bromo, A is hydroxyl and $R^2$ is methyl, and the radical $R^1$ for each compound corresponds to one line of Table A Table 183
Compounds of the formula I where $(X)_m$ is 4-bromo, A is hydroxyl and $R^2$ is methoxy, and the radical $R^1$ for each compound corresponds to one line of Table A Table 184
Compounds of the formula I where $(X)_m$ is 4-bromo, A is hydroxyl and $R^2$ is cyano, and the radical $R^1$ for each compound corresponds to one line of Table A Table 185
Compounds of the formula I where $(X)_m$ is 5-bromo, A is hydroxyl and $R^2$ is hydrogen, and the radical $R^1$ for each compound corresponds to one line of Table A Table 186

Compounds of the formula I where $(X)_m$ is 5-bromo, A is hydroxyl and $R^2$ is methyl, and the radical $R^1$ for each compound corresponds to one line of Table A Table 187

Compounds of the formula I where $(X)_m$ is 5-bromo, A is hydroxyl and $R^2$ is methoxy, and the radical $R^1$ for each compound corresponds to one line of Table A Table 188

Compounds of the formula I where $(X)_m$ is 5-bromo, A is hydroxyl and $R^2$ is cyano, and the radical $R^1$ for each compound corresponds to one line of Table A Table 189

Compounds of the formula I where $(X)_m$ is 3-nitro, A is hydroxyl and $R^2$ is hydrogen, and the radical $R^1$ for each compound corresponds to one line of Table A Table 190

Compounds of the formula I where $(X)_m$ is 3-nitro, A is hydroxyl and $R^2$ is methyl, and the radical $R^1$ for each compound corresponds to one line of Table A Table 191

Compounds of the formula I where $(X)_m$ is 3-nitro, A is hydroxyl and $R^2$ is methoxy, and the radical $R^1$ for each compound corresponds to one line of Table A Table 192

Compounds of the formula I where $(X)_m$ is 3-nitro, A is hydroxyl and $R^2$ is cyano, and the radical $R^1$ for each compound corresponds to one line of Table A Table 193

Compounds of the formula I where $(X)_m$ is 4-nitro, A and $R^2$ are hydrogen, and the radical $R^1$ for each compound corresponds to one line of Table A Table 194

Compounds of the formula I where $(X)_m$ is 4-nitro, A is hydroxyl and $R^2$ is methyl, and the radical $R^1$ for each compound corresponds to one line of Table A Table 195

Compounds of the formula I where $(X)_m$ is 4-nitro, A is hydroxyl and $R^2$ is methoxy, and the radical $R^1$ for each compound corresponds to one line of Table A Table 196

Compounds of the formula I where $(X)_m$ is 4-nitro, A is hydroxyl and $R^2$ is cyano, and the radical $R^1$ for each compound corresponds to one line of Table A Table 197

Compounds of the formula I where $(X)_m$ is 5-nitro, A is hydroxyl and $R^2$ is hydrogen, and the radical $R^1$ for each compound corresponds to one line of Table A Table 198

Compounds of the formula I where $(X)_m$ is 5-nitro, A is hydroxyl and $R^2$ is methyl, and the radical $R^1$ for each compound corresponds to one line of Table A Table 199

Compounds of the formula I where $(X)_m$ is 5-nitro, A is hydroxyl and $R^2$ is methoxy, and the radical $R^1$ for each compound corresponds to one line of Table A Table 200

Compounds of the formula I where $(X)_m$ is 5-nitro, A is hydroxyl and $R^2$ is cyano, and the radical $R^1$ for each compound corresponds to one line of Table A

TABLE A

| No. | $R^1$ | $R^a$ |
|---|---|---|
| A-1 | c-$C_6H_{11}$ | — |
| A-2 | c-$C_6H_{10}$ | 1-Cl |
| A-3 | c-$C_6H_{10}$ | 2-Cl |
| A-4 | c-$C_6H_{10}$ | 3-Cl |
| A-5 | c-$C_6H_{10}$ | 4-Cl |
| A-6 | c-$C_6H_{10}$ | 1-Br |
| A-7 | c-$C_6H_{10}$ | 2-Br |
| A-8 | c-$C_6H_{10}$ | 3-Br |
| A-9 | c-$C_6H_{10}$ | 4-Br |
| A-10 | c-$C_6H_{10}$ | 1-$NO_2$ |
| A-11 | c-$C_6H_{10}$ | 2-$NO_2$ |
| A-12 | c-$C_6H_{10}$ | 3-$NO_2$ |
| A-13 | c-$C_6H_{10}$ | 4-$NO_2$ |
| A-14 | c-$C_6H_{10}$ | 1-CN |
| A-15 | c-$C_6H_{10}$ | 2-CN |
| A-16 | c-$C_6H_{10}$ | 3-CN |
| A-17 | c-$C_6H_{10}$ | 4-CN |
| A-18 | c-$C_6H_{10}$ | 1-$CH_3$ |
| A-19 | c-$C_6H_{10}$ | 2-$CH_3$ |
| A-20 | c-$C_6H_{10}$ | 3-$CH_3$ |
| A-21 | c-$C_6H_{10}$ | 4-$CH_3$ |
| A-22 | c-$C_6H_9$ | 2,4-$(Cl)_2$ |
| A-23 | c-$C_6H_9$ | 2,4-$(Br)_2$ |
| A-24 | c-$C_6H_9$ | 2,4-$(NO_2)_2$ |
| A-25 | c-$C_6H_9$ | 2,4-$(CH_3)_2$ |
| A-26 | $C_6H_5$ | — |
| A-27 | $C_6H_4$ | 2-Cl |
| A-28 | $C_6H_4$ | 3-Cl |
| A-29 | $C_6H_4$ | 4-Cl |
| A-30 | $C_6H_4$ | 2-Br |
| A-31 | $C_6H_4$ | 3-Br |
| A-32 | $C_6H_4$ | 4-Br |
| A-33 | $C_6H_4$ | 2-$NO_2$ |
| A-34 | $C_6H_4$ | 3-$NO_2$ |
| A-35 | $C_6H_4$ | 4-$NO_2$ |
| A-36 | $C_6H_4$ | 2-CN |
| A-37 | $C_6H_4$ | 3-CN |
| A-38 | $C_6H_4$ | 4-CN |
| A-39 | $C_6H_4$ | 2-$CH_3$ |
| A-40 | $C_6H_4$ | 3-$CH_3$ |
| A-41 | $C_6H_4$ | 4-$CH_3$ |
| A-42 | $C_6H_4$ | 4-$CH_2CH_3$ |
| A-43 | $C_6H_4$ | 4-$CH_2CH_2CH_3$ |
| A-44 | $C_6H_4$ | 4-$CH(CH_3)_2$ |
| A-45 | $C_6H_4$ | 4-$CH_2CH_2CH_2CH_3$ |
| A-46 | $C_6H_4$ | 4-$CH_2CH(CH_3)_2$ |
| A-47 | $C_6H_4$ | 4-$C(CH_3)_3$ |
| A-48 | $C_6H_4$ | 4-$C_6H_5$ |
| A-49 | $C_6H_4$ | 4-(2-Cl)—$C_6H_4$ |
| A-50 | $C_6H_4$ | 4-(3-Cl)—$C_6H_4$ |
| A-51 | $C_6H_4$ | 4-(4-Cl)—$C_6H_4$ |
| A-52 | $C_6H_4$ | 4-(2-Br)—$C_6H_4$ |
| A-53 | $C_6H_4$ | 4-(3-Br)—$C_6H_4$ |
| A-54 | $C_6H_4$ | 4-(4-Br)—$C_6H_4$ |
| A-55 | $C_6H_4$ | 4-(2-$NO_2$)—$C_6H_4$ |
| A-56 | $C_6H_4$ | 4-(3-$NO_2$)—$C_6H_4$ |
| A-57 | $C_6H_4$ | 4-(4-$NO_2$)—$C_6H_4$ |
| A-58 | $C_6H_4$ | 4-(2-CN)—$C_6H_4$ |
| A-59 | $C_6H_4$ | 4-(3-CN)—$C_6H_4$ |
| A-60 | $C_6H_4$ | 4-(4-CN)—$C_6H_4$ |
| A-61 | $C_6H_4$ | 4-(2-$CH_3$)—$C_6H_4$ |
| A-62 | $C_6H_4$ | 4-(3-$CH_3$)—$C_6H_4$ |
| A-63 | $C_6H_4$ | 4-(4-$CH_3$)—$C_6H_4$ |
| A-64 | $C_6H_4$ | 4-(2,4-$Cl_2$)—$C_6H_3$ |
| A-65 | $C_6H_4$ | 4-(2,4-$Br_2$)—$C_6H_3$ |
| A-66 | $C_6H_4$ | 4-[2,4-$(NO_2)_2$]—$C_6H_3$ |
| A-67 | $C_6H_4$ | 4-[2,4-$(CH_3)_2$]—$C_6H_3$ |
| A-68 | 2-thiophene | — |
| A-69 | 2-pyrazine | — |
| A-70 | 2-pyrimidine | — |
| A-71 | 4-pyrimidine | — |
| A-72 | 2-pyridine | — |
| A-73 | 3-pyridine | — |
| A-74 | 4-pyridine | — |
| A-75 | 5-pyridine | — |

The compounds I are suitable as fungicides. They are distinguished by an outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soybean, coffee, sugar cane, grapevine, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,

*Botrytis cinerea* (gray mold) on strawberries, vegetables, ornamentals and grapevines,

*Cercospora arachidicola* on peanuts,

*Erysiphe cichoracearum* and *Sphaerotheca fuliginea* on cucurbits,

*Erysiphe graminis* (powdery mildew) on cereals,

Fusarium- and Verticillium species on a variety of plants,

Helminthosporium species on cereals,

Mycosphaerella species on bananas and peanuts,

*Phytophthora infestans* on potatoes and tomatoes,

*Plasmopara viticola* on grapevines,

*Podosphaera leucotricha* on apples,

*Pseudocercosporella herpotrichoides* on wheat and barley,

Pseudoperonospora species on hops and cucumbers,

Puccinia species on cereals,

*Pyricularia oryzae* on rice,

Rhizoctonia species on cotton, rice and turf,

*Septoria nodorum* on wheat,

*Uncinula necator* on grapevines,

Ustilago species on cereals and sugar cane, and

Venturia species (scab) on apples and pears.

Moreover, the compounds I are suitable for controlling harmful fungi such as *Paecilomyces variotii* in the protection of materials (e.g. wood, paper, paint dispersions, fibers and fabrics) and in the protection of stored products.

The compounds I are applied by treating the fungi, or the plants, seed, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the application rates are from 0.01 to 2.0 kg of active ingredient per ha, depending on the nature of the desired effect.

In the treatment of seeds, amounts of active ingredient of from 0.001 to 0.1 g, preferably 0.01 to 0.05 g, are generally required per kilogram of seed.

When used in the protection of materials or stored products, the application rate of active ingredient depends on the nature of the field of application and on the desired effect. Application rates conventionally used in the protection of materials are, for example, from 0.001 g to 2 kg, preferably from 0.005 g to 1 kg, of active ingredient per cubic meter of material treated.

The compounds I can be converted into the customary formulations, e.g. solutions, emulsions, suspensions, dusts, powders, pastes and granules. The use form depends on the particular purpose; it is intended to ensure in each case a fine and uniform distribution of the compound according to the invention.

The formulations are prepared in a known manner, e.g. by extending the active ingredient with solvents and/or carriers, if desired using emulsifiers and dispersants, it also being possible to use other organic solvents as cosolvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanones), amines (e.g. ethanolamine, N,N-dimethylformamide) and water; carriers such as ground natural minerals (e.g. kaolins, clays, talc, chalk) and ground synthetic minerals (e.g. highly disperse silica, silicates); emulsifiers such as nonionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol or formaldehyde, polyoxyethylene octylphenol ether, ethoxylated isooctylphenol, octylphenol, nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. N,N-dimethylformamide, dimethyl sulfoxide, N-methylpyrrolidone and water.

Powders, materials for spreading and dusts can be prepared by mixing or concomitantly grinding the active substances with a solid carrier.

Granules, e.g. coated granules, impregnated granules, homogeneous granules, can be prepared by binding the active ingredients on solid carriers. Examples of solid carriers are mineral earths such as silicas, silica gels, talc, kaolin, attaclay, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders and other solid carriers.

In general, the formulations comprise between 0.01 and 95% by weight, preferably between 0.1 and 90% by weight, of the active ingredient. The active ingredients are employed in a purity of from 90% to 100%, preferably from 95% to 100% (according to NMR spectrum).

The following are examples of formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of active ingredient with good adhesion properties (active ingredient content 23% by weight).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (active ingredient compound 9% by weight).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (active ingredient content 16% by weight).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (active ingredient content 80% by weight).

VI. 90 parts by weight of a compound according to the invention are mixed with 10 parts by weight of N-methyl-α-pyrrolidone, which gives a solution which is suitable for use in the form of microdrops (active ingredient content 90% by weight).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion comprising 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture comprising 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; it is intended to ensure in each case the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are between 0.0001 and 10%, preferably between 0.01 and 1%.

The active ingredients may also be used successfully in the ultra-low-volume method (ULV), it being possible to apply formulations comprising over 95% by weight of active ingredient, or even to apply the active ingredient without additives.

Various types of oils, herbicides, fungicides, other pesticides, or bactericides may be added to the active ingredients, if appropriate immediately prior to use (tank mix). These agents can be admixed with the agents according to the invention in a weight ratio of 1:10 to 10:1.

In the use form as fungicides, the compositions according to the invention can also be present together with other active ingredients, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]-quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1, 2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane;

amines such as 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine;

azoles such as 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;

strobilurins such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoxy imino-[α-(2-phenoxyphenyl)]acetamide, N-methyl E-methoxyimino-[α-(2,5-dimethylphenoxy)-o-tolyl] acetamide; methyl E-2-{2-[2-trifluoromethylpyridyl-6-]oxymethyl]phenyl}-3-methoxyacrylate, methyl (E,E)-methoximino-{2-[1-(3-trifluoromethylphenyl) ethylideneaminooxymethyl]phenyl}acetate, methyl N-(2-{[1-(4-chlorophenyl)-1H-pyrazol-3-yl]-oxymethyl}phenyl)N-methoxycarbamate, anilinopyrimidines such as N-(4,6-dimethylpyrimidin-2-yl)aniline, N-[4-methyl-6-(1-propynyl)pyrimidin-2-yl] aniline, N-[4-methyl-6-cyclopropylpyrimidin-2-yl] aniline;

phenylpyrroles such as 4-(2,2-difluoro-1,3-benzodioxol-4-yl)pyrrole-3-carbonitrile;

cinnamamides such as 3-(4-chlorophenyl)-3-(3,4-dimethoxyphenyl)acryloylmorpholine;

and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl) alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl) methylsilyl)methyl)-1H-1,2,4-triazole.

SYNTHESIS EXAMPLES

With due modification of the starting compounds, the protocols shown in the synthesis examples below were used for obtaining further compounds I. The resulting compounds, together with physical data, are listed in the tables which follow.

Example 1

Preparation of Methyl 3-(1,1-dibromo) methylacetoxysalicylate 53 g (0.25 mol) of methyl 3-methylacetoxysalicylate, 95 g (0.53 mol) of N-bromosuccinimide and a spatula-tipfull of azobisisobutyronitrile (AIBN) as free-radical initiator were irradiated in 600 ml of tetrachlorocarbon with a UV lamp (500 W). The temperature of the reaction mixture climbed for approximately 6 minutes to reflux. After a further 15 minutes' irradiation, the mixture was allowed to cool to room temperature. The succinimide which had precipitated was filtered off and washed with $CCl_4$. The filtrate was freed from solvent. Following silica gel chromatography (cyclohexane:methyl tert-butyl ether [MTBE] 5:1), 72 g of the title compound were obtained, which corresponds to 78% of theory.

Example 2

Preparation of Methyl 3-formyl-2-hydroxybenzoate 63 ml of concentrated sulfuric acid were added dropwise at approximately 20 to 25° C. to a solution of 64 g (0.17 mol) of the dibromide of Example 1 in 500 ml of anhydrous methanol. The temperature of the reaction solution was kept at 30° C. by cooling. After the mixture had been stirred for 30 minutes at 20 to 25° C., it was heated for 3 hours to 50° C. The reaction mixture was stirred into approximately 3.5 l of water. The precipitate was filtered off and washed with water and then with a pentane/MTBE mixture (5:1). After drying, 25 g of the title compound were obtained, which corresponds to 81% of theory. (m.p. 82° C.)

Example 3

Preparation of N-methyl-3-methyliminomethyl-2-hydroxybenzamide 50 g of 40% strength aqueous methylamine solution were added to a solution of 12 g (65 mmol) of the aldehyde from Example 2 in 100 ml of tetrahydrofuran (THF). After the mixture had been stirred for 2 hours at 50° C., the solvent was distilled off. This gave 14 g of the title compound, which corresponds to 99% of theory.

Example 4

Preparation of N-methyl-3-formyl-2-hydroxybenzamide 60 ml of concentrated aqueous hydrochloric acid were added at 20 to 25° C. to 14 g (65 mmol) of the methylamide of Example 3 in a mixture of 120 ml of THF and 100 ml of water. After the reaction mixture had been stirred for approximately 14 hours at 20 to 25° C., it was taken up in MTBE and washed with water. After drying, the solvent was distilled off. 8 g of the title compound, which corresponded to 71% of theory, were obtained from the residue. (m.p.: 129–131° C.)

Example 5

Preparation of Methyl 2-hydroxy-3-(p-tolylhydrazonomethyl)benzoate [I-2]

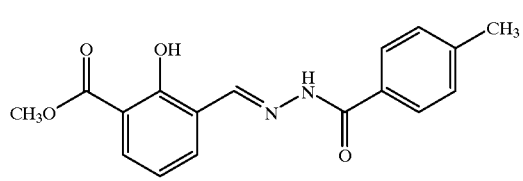

A solution of 1.1 g (6 mmol) of the aldehyde of Example 2 in 30 ml of anhydrous methanol was reacted with 0.9 g (6 mmol) of p-toluenebenzohydrazide with acid catalysis (para-toluenesulfonic acid). After the reaction mixture had been stirred for approximately 14 hours at 20 to 25° C., it was freed from the solvent. 1.9 g of the title compound, which corresponded to 99% of theory, were obtained from the residue. (m.p. 134–137° C.)

Example 6

Preparation of N-methyl-2-hydroxy-3-(p-tolylhydrazonomethyl)benzamide [I-13]

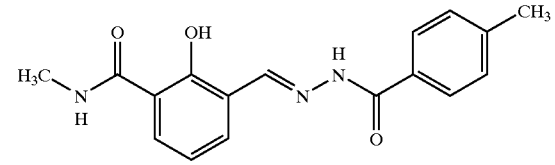

A soluton of 200 mg (1 mmol) of the aldehyde of Example 4 in 30 ml of anhydrous methanol was reacted with 140 mg (1 mmol) of p-toluenebenzohydrazide with acid catalysis (para-toluenesulfonic acid). After the reaction mixture had been stirred for approximately 14 hours at 20 to 25° C., it was freed from the solvent. 340 mg of the title compound, which corresponded to 99% of theory, were obtained from the residue. (m.p. 108–125° C.)

TABLE I

Compounds of the formula I

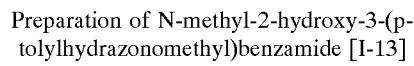

| No. | A | $(X)_m$ | $R^1$ | $R^2$ | Physical data (m.p. [° C.]) |
|---|---|---|---|---|---|
| I-1 | OCH$_3$ | H | C$_6$H$_5$ | H | 188–191 |
| I-2 | OCH$_3$ | H | (4-CH$_3$)—C$_6$H$_4$ | H | 134–137 |
| I-3 | OCH$_3$ | H | (4-Cl)—C$_6$H$_4$ | H | 213–219 |
| I-4 | OCH$_3$ | H | (4-Br)—C$_6$H$_4$ | H | 213–218 |
| I-5 | OCH$_3$ | H | (4-OH)—C$_6$H$_4$ | H | 239–247 |
| I-6 | OCH$_3$ | H | (4-NO$_2$)—C$_6$H$_4$ | H | 255–260 |
| I-7 | OCH$_3$ | H | (4-F)—C$_6$H$_4$ | H | 188–192 |
| I-8 | OCH$_3$ | H | (4-NH$_2$)—C$_6$H$_4$ | H | 109–115 |
| I-9 | OCH$_3$ | H | (3-CH$_3$)—C$_6$H$_4$ | H | 173–178 |
| I-10 | OCH$_3$ | H | (3-Cl)—C$_6$H$_4$ | H | 169–172 |
| I-11 | OCH$_3$ | H | (3-OH)—C$_6$H$_4$ | H | 150–155 |
| I-12 | OCH$_3$ | H | (3-NO$_2$)—C$_6$H$_4$ | H | 165–169 |
| I-13 | OCH$_3$ | H | (3-F)—C$_6$H$_4$ | H | 123–126 |
| I-14 | OCH$_3$ | H | (3-NH$_2$)—C$_6$H$_4$ | H | 123–130 |
| I-15 | OCH$_3$ | H | (3-Br)—C$_6$H$_4$ | H | 190–193 |
| I-16 | NHCH$_3$ | H | C$_6$H$_5$ | H | 108–125 |
| I-17 | NHCH$_3$ | H | (4-CH$_3$)—C$_6$H$_4$ | H | 94–106 |
| I-18 | NHCH$_3$ | H | (4-Cl)—C$_6$H$_4$ | H | 206–208 |
| I-19 | NHCH$_3$ | H | (4-Br)—C$_6$H$_4$ | H | 215–223 |
| I-20 | NHCH$_3$ | H | (4-OH)—C$_6$H$_4$ | H | 262–265 |
| I-21 | NHCH$_3$ | H | (4-NO$_2$)—C$_6$H$_4$ | H | 263–268 |
| I-22 | NHCH$_3$ | H | (4-F)—C$_6$H$_4$ | H | 210–220 |
| I-23 | NHCH$_3$ | H | (4-NH$_2$)—C$_6$H$_4$ | H | 234–236 |
| I-24 | NHCH$_3$ | H | (3-CH$_3$)—C$_6$H$_4$ | H | 160–164 |
| I-25 | NHCH$_3$ | H | (3-Cl)—C$_6$H$_4$ | H | 121–130 |
| I-26 | NHCH$_3$ | H | (3-Br)—C$_6$H$_4$ | H | 137–142 |
| I-27 | NHCH$_3$ | H | (3-OH)—C$_6$H$_4$ | H | 250–253 |
| I-28 | NHCH$_3$ | H | (3-NO$_2$)—C$_6$H$_4$ | H | 240–245 |
| I-29 | NHCH$_3$ | H | (3-F)—C$_6$H$_4$ | H | 180–190 |
| I-30 | NHCH$_3$ | H | (3-NH$_2$)—C$_6$H$_4$ | H | 234–236 |
| I-31 | NH$_2$ | H | C$_6$H$_5$ | H | 223–225 |
| I-32 | NH$_2$ | H | (4-CH$_3$)—C$_6$H$_4$ | H | 244–246 |
| I-33 | NH$_2$ | H | (4-Cl)—C$_6$H$_4$ | H | 245–247 |
| I-34 | NH$_2$ | H | (4-Br)—C$_6$H$_4$ | H | 213–214 |
| I-35 | NH$_2$ | H | (4-OH)—C$_6$H$_4$ | H | 260–263 |
| I-36 | NH$_2$ | H | (4-NO$_2$)—C$_6$H$_4$ | H | 270–273 |
| I-37 | NH$_2$ | H | (4-F)—C$_6$H$_4$ | H | 212–215 |
| I-38 | NH$_2$ | H | (4-NH$_2$)—C$_6$H$_4$ | H | 252–253 |
| I-39 | NH$_2$ | H | (3-CH$_3$)—C$_6$H$_4$ | H | 227–230 |
| I-40 | NH$_2$ | H | (3-Cl)—C$_6$H$_4$ | H | 243–245 |
| I-41 | NH$_2$ | H | (3-Br)—C$_6$H$_4$ | H | 250–251 |
| I-42 | NH$_2$ | H | (3-OH)—C$_6$H$_4$ | H | 251–252 |
| I-43 | NH$_2$ | H | (3-NO$_2$)—C$_6$H$_4$ | H | 256–258 |
| I-44 | NH$_2$ | H | (3-F)—C$_6$H$_4$ | H | 247–256 |
| I-45 | NH$_2$ | H | (3-NH$_2$)—C$_6$H$_4$ | H | 240–242 |

Examples for the Action Against Harmful Fungi

The fungicidal action of the compounds of the formula I was demonstrated by the following experiments:

The active ingredients, separately or together, were prepared as a 10% emulsion in a mixture of 70% by weight of cyclohexanone, 20% by weight of Nekanil® LN (Lutensol® AP6, wetter with emulsifying and dispersant action based on ethoxylated alkylphenols) and 10% by weight of Wettol® EM (nonionic emulsifier based on ethoxylated castor oil) and the preparations were diluted with water to give the desired concentration.

Use Example 1

Activity Against *Alternaria solani* on Tomatoes

Leaves of potted plants cv. "Große Fleischtomate St. Pierre" were sprayed to runoff point with an aqueous suspension made with a stock solution of 10% of active ingredient, 63% of cyclohexanone and 27% of emulsifier. Next day, the leaves were infected with an aqueous *Alternaria solani* zoospore suspension in 2% Biomalz solution at a density of $0.17 \times 10^6$ spores/ml. The plants were subsequently placed into a water-vapor-saturated chamber at temperatures between 20 and 22° C. After 5 days, the lesions on the untreated, but infected, control plants had developed to such an extent that it was possible to score the disease level visually in percent.

In this test, the plants treated with 250 ppm of the active ingredients No. I-1, I-2, I-3, I-14, I-26 and I-31 of Table I showed a disease level of not more than 15%, while the untreated plants showed a disease level of 90%.

Use Example 2

Activity Against *Botrytis cinerea* on Sweet Pepper Leaves

Sweet pepper seedlings cv. "Neusiedler Ideal Elite" were sprayed to runoff point with an aqueous active ingredient preparation made with a stock solution of 10% of active ingredient, 63% of cyclohexanone and 27% of emulsifier, after 4–5 leaves had developed properly. Next day, the treated plants were inoculated with a spore suspension of *Botrytis cinerea* which contained $1.7 \times 10^6$ spores/ml in a 2% strength aqueous Biomalz solution. The test plants were subsequently placed into a controlled environment cabinet at 22 to 24° C. and high atmospheric humidity. After 5 days, it was possible to determine the extent of the fungal disease on the leaves visually in percent.

In this test, the plants treated with 250 ppm of the active ingredients No. I-1 to I-4, I-7, I-9, I-14 and I-25 of Table I showed a disease level of not more than 20%, while the disease level of the untreated plants was 100%.

Use Example 3

Activity Against *Phytophthora infestans* on Tomatoes

Leaves of potted plants cv. "Große Fleischtomate St. Pierre" were sprayed to runoff point with an aqueous suspension made with a stock solution of 10% of active ingredient, 63% of cyclohexanone and 27% of emulsifier. Next day, the leaves were infected with a cold aqueous *Phytophthora infestans* zoospore suspension at a density of $0.25 \times 10^6$ spores/ml. The plants were subsequently placed into a water-vapor-saturated chamber at temperatures between 18 and 20° C. After 6 days, the blight on the untreated, but infected, control plants had developed to such an extent that it was possible to score the disease level visually in percent.

In this test, the plants treated with 250 ppm of the active ingredients No. I-1, I-2, I-7, I-9, I-10, I-11 and I-13 of Table I showed a disease level of not more than 20%, while the untreated plants showed a disease level of 80%.

We claim:

1. A salicylic acid derivative of the formula I

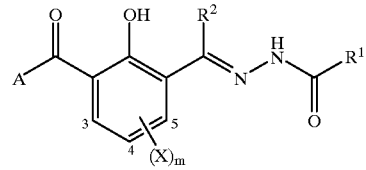

where the index and the substituents are as follows:

X is halogen, $NO_2$, cyano, $C_1$–$C_4$-alkyl or $C_1$–$C_4$-alkoxy;

m is 0, 1, 2 or 3, it being possible for the substituents X to differ from each other if n is greater than 1;

A is OH, $C_1$–$C_4$-alkoxy, $NH_2$, $NHCH_3$ or $N(CH_3)_2$;

$R^1$ is phenyl, unsubstituted or substituted by one to three radicals $R^a$:

$R^a$ is cyano, nitro, amino, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, phenyl, phenoxy, benzyl, benzyloxy, 5- or 6-membered heterocyclyl, 5- or 6-membered hetaryl, 5- or 6-membered hetaryloxy, $C(=NOR^\alpha)$—$OR^6$ or $OC(R^\alpha)_2$—$C(R^6)$=$NOR^6$, any cyclic radicals of $R^a$, in turn, being unsubstituted or substituted by one to three radicals $R^b$:

$R^b$ is cyano, nitro, halogen, hydroxyl, amino, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkenyl, phenyl, phenoxy, phenylthio, benzyl, benzyloxy, 5- or 6-membered heterocyclyl, 5- or 6-membered hetaryl, 5- or 6-membered hetaryloxy or $C(=NOR^\alpha)$—$OR^6$;

$R^\alpha$, $R^6$ is hydrogen or $C_1$–$C_6$-alkyl;

$R^2$ is hydrogen, cyano, $C_1$–$C_6$-alkyl, $C_2$–$C_6$-alkenyl, $C_2$–$C_6$-alkynyl, $C_1$–$C_6$-haloalkyl, $C_1$–$C_6$-alkoxy or $C_1$–$C_6$-alkylthio, the hydrocarbon radicals being unsubstituted or partially or fully halogenated or it being possible for them to have attached to them one to three groups $R^c$:

$R^c$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_3$–$C_6$-alkenyloxy, $C_3$–$C_6$-alkynyloxy or $C_1$–$C_4$-alkylenedioxy which can be halogenated.

2. A compound of the formula I as claimed in claim 1 where m is zero, and X, A, $R^1$ and $R^2$ are as defined in claim 1.

3. A compound of the formula I as claimed in claim 1 where m is 1 and X is in the 4-position, and X, A, $R^1$ and $R^2$ are as defined in claim 1.

4. A compound of the formula I as claimed in claim 1 where
A is methoxy, $NH_2$, $NHCH_3$ or $N(CH_3)_2$; and
$R^2$ is hydrogen or methyl,
X, m and $R^1$ are as defined in claim 1.

5. A compound of the formula I as claimed in claim 1 where $R^2$ is hydrogen, and X, m, A and $R^1$ are as defined in claim 1.

6. A process for the preparation of compounds of the formula I as claimed in claim 1 by means of halogenation, under free-radical conditions, of salicylic esters of the formula II

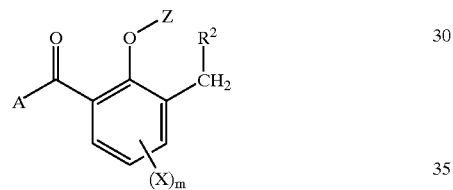

where A is $C_1$–$C_4$-alkoxy and Z is a protecting group which can be eliminated under acidic conditions, to give dihalides of the formula

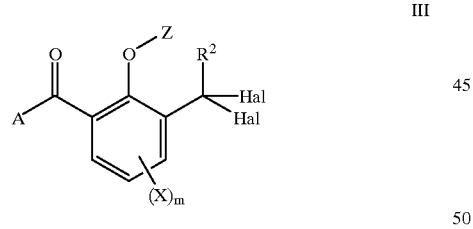

where Hal is chlorine or bromine, oxidation and elimination of the protecting group of III under acidic conditions to give compounds of the formula IV,

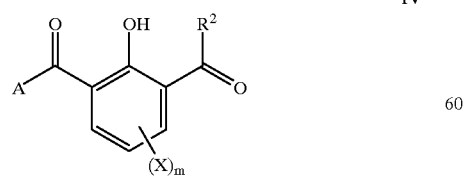

and, for the preparation of compounds I where A is $NH_2$ or $N(CH_3)_2$, amidation of IV with ammonia or methylamine to give salicylamides of the formula IV.1

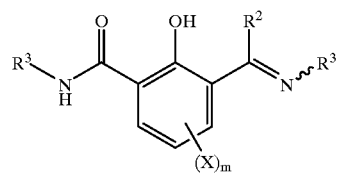

where $R^3$ is hydrogen or methyl, elimination of the imino group from formula IV.1 to give keto compounds of the formula IV.2

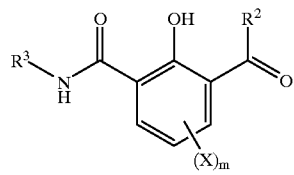

and, for the preparation of compounds I where A is $N(CH_3)_2$, amidation of IV with dimethylamine to give salicylamides of the formula IV.3,

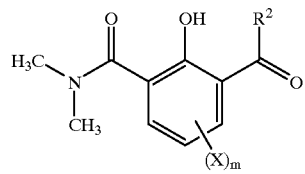

and, for the preparation of compounds of the formula I where A is hydroxyl, hydrolysis of IV to give compounds IV.4

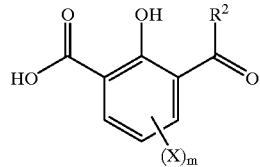

wherein in each of formulas II, III, IV, IV.1, IV.2, IV.3 and IV.4, X and m are as defined in claim 1, and condensation of IV, IV.2, IV.3 or IV.4 with hydrazides of the formula V

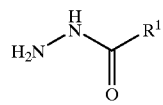

to give compounds of the formula I.

7. The process as claimed in claim 6 where, in formulae II and III, Z is an acetyl group, and A and Hal are as defined in claim 6.

8. A composition which is suitable for controlling phytopathogenic harmful fungi, comprising a solid or liquid carrier and a compound of the formula I as claimed in claim 1, wherein all of the substituents of formula I are as defined in claim 1.

9. A method of controlling phytopathogenic harmful fungi, which comprises treating the fungi or the materials, plants, the soil or seeds to be protected against fungal infection with an effective amount of a compound of the formula I as claimed in claim 1, wherein all of the substituents of formula I are as defined in claim 1.

\* \* \* \* \*